United States Patent [19]

Kossoff et al.

[11] 4,078,435
[45] Mar. 14, 1978

[54] SIMULTANEOUS DISPLAY OF COMPOUND AND SIMPLE ULTRASOUND SCANS

[75] Inventors: George Kossoff; David Arthur Carpenter, both of Northbridge, Australia

[73] Assignee: The Commonwealth of Australia C/-The Department of Health, Phillip, Australia

[21] Appl. No.: 715,288

[22] Filed: Aug. 18, 1976

[30] Foreign Application Priority Data

Aug. 20, 1975 Australia ............................. PC2856

[51] Int. Cl.² ............................................ G01N 29/04
[52] U.S. Cl. ........................................ 73/621; 73/626; 128/2 V
[58] Field of Search ........................... 73/67.8 S, 67.9; 128/2 V

[56] References Cited

U.S. PATENT DOCUMENTS 3,939,696  2/1976  Kossoff ............................. 73/67.8 S
3,996,792  12/1976  Kubota et al. ..................... 73/67.8 S

*Primary Examiner*—James J. Gill

[57] ABSTRACT

A technique of displaying information obtained by ultrasonic echoscopic examination of an object which comprises the steps of transmitting pulses of ultrasonic energy along a plurality of beams into the object and receiving echoes of said pulses reflected along the beams by acoustic impedance discontinuities within the object, the beams being directed from a plurality of spaced positions relative to the object and along a plurality of beam directions at each position, comprises forming a first display of information representative of the position of acoustic impedance discontinuities within the object from the echoes received along the plurality of beams as a compound scan of the object, and forming a second display of information from echoes received along selected beams of the plurality of beams as a simple scan of the object.

5 Claims, 3 Drawing Figures

SIMULTANEOUS DISPLAY OF COMPOUND AND SIMPLE ULTRASOUND SCANS

This invention relates to the technique of ultrasonic echoscopy of objects and in particular to means for providing a more complete and diagnostically useful display of the results of the examination of the objects. It is particularly, but not solely, directed to the use of this technique in medical diagnostic examination.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line "A mode" or as an intensity change "B mode". In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. The application of this technique is now widely investigated and is described, for example, by D.E. Robinson in Proceedings of the Institution of Radio and Electronics Engineers Australia, Vol. 31, No. 11, pages 385–392, November, 1970: "The Application of Ultrasound in Medical Diagnosis". As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients' condition, however, particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross-section as previously described.

In one presently known form of ultrasonic diagnostic examination, a single transducer is used and it is physically moved to various positions around the patient. At each of these positions the beam is swept with an oscillatory motion while constrained to remain within a single plane by mechanical oscillation of the transducer, to obtain the required scan pattern. By the use of suitable deflection circuits, for example, in a cathode ray display tube, a line is caused to follow the motions of the beam axis and echoes within the part examined are thus displayed in their correct geometrical positions. By way of example, for transverse sections, the transducer may be moved horizontally in a 150° arc around a patient who is substantially erect while undergoing ± 15° oscillations and for longidutinal sections the transducer may be moved vertically while undergoing ± 30° oscillations.

In the types of scanning motion of the transducer described above any point within the patient being examined will be viewed a number of different times by the transducer. This will occur as the transducer moves linearly or radially around the patient and scans from a number of different directions. This type of scan produces the most complete picture of the anatomy and is called a compound scan. It has also been shown that considerable information can be obtained from a simpler scan such as a linear scan in which the transducer is moved linearly past the patient or a sector scan in which the transducer is oscillated about a fixed origin position to scan the patient. The important feature of these simple scans is that any point within the organ is viewed only once. This allows enhancement or shadowing of echoes behind a suspected area within the organ to be displayed. Resolution is not affected by local changes of velocity within the organ or by misalignment of the equipment. Also refraction effects and movement of the organ produce distortion but not loss of resolution of the echogram.

At present a compound scan of an object may be carried out first and then a simple linear or sector scan of the area of interest. This can lead to problems due to any movement of the object, particularly an organ, between the time of these two scans due to patient movement, respiration or cardiac movement.

It is an object of the present invention to provide means whereby information obtained by ultrasonic examination of an object may be readily and accurately displayed for use while avoiding the problems discussed above as arising from the use of two scans.

According to the present invention there is provided a method of displaying information obtained by ultrasonic echoscopic examination of an object, said examination comprising the steps of transmitting pulses of ultrasonic energy along a plurality of beams into the said object and receiving echoes of said pulses reflected along said beams by acoustic impedance discontinuities within the object, said beams being directed from a plurality of spaced positions relative to said object and along a plurality of beam directions at each said position, which method comprises forming a first display of information representative of the position of acoustic impedance discontinuities within said object from said echoes received along said plurality of beams, and forming a second display of information from echoes received along selected beams of said plurality of beams.

In another aspect, the invention provides apparatus for the ultrasonic echoscopic examination of an object, comprising transducer means for transmitting pulses of ultrasonic energy along a plurality of beams into the said object and receiving echoes of said pulsed reflected along said beams by acoustic impedance discontinuities within the object, said transducer means directing said beams from a plurality of spaced positions relative to said object and along a plurality of beam directions at each said position, means for forming a first display of information representative of the position of acoustic impedance discontinuities within said object from said echoes received along said plurality of beams, means for selecting beams from said plurality of beams, and means for forming a second display of information from echoes received along said selected beams.

In general, the present invention enables simultaneous display of both a compound and a simple scan. This is possible as the compound scan is, in effect, made up from the combination of a number of simple scans. Furthermore, provided that a display or storage facility with high enough resolution to display both scans simultaneously is available, the required simple scan can be separated from the compound scan without degradation of either scan.

An example of a high quality display system is that of a scan converter system or dual oscilloscope units which can fulfill the requirements and the electronic circuitry to be described hereinafter facilitates the removal and re-display of a simple scan from a compound scan. There are a number of different ways in which the present invention may be effectively performed. In one such alternative, one of the simple scans which goes to make up a compound scan can be simply removed and displayed to one side of the compound scan. Alternatively, where a single transducer echoscope is used in which many more ultrasound pulses are deployed than is necessary to display the object, it is possible to remove every second pulse during the simple scan that is desired and shift it to one side to display the separate simple scan. This latter alternative has the advantage that virtually no information within the simple scan is lost from the compound scan. In the alternative in which a multi-transducer echoscope is utilised to perform the invention, each transducer may execute a simple scan but the combination of a number of these simple scans is used to produce a compound scan and only the minimum number of pulses needed to produce a scan is used. In this alternative, the transducer which is providing the simple scan that is desired is pulsed twice as often as normal so one pulse is used for the compound scan and one for the simple scan which is to be displayed at one side. This again ensures that no information is lost from the compound scan.

Further features of the present invention will be apparent from the accompanying drawings which illustrate, by way of example only, an embodiment of the present invention. In the drawings.

Figure 1:
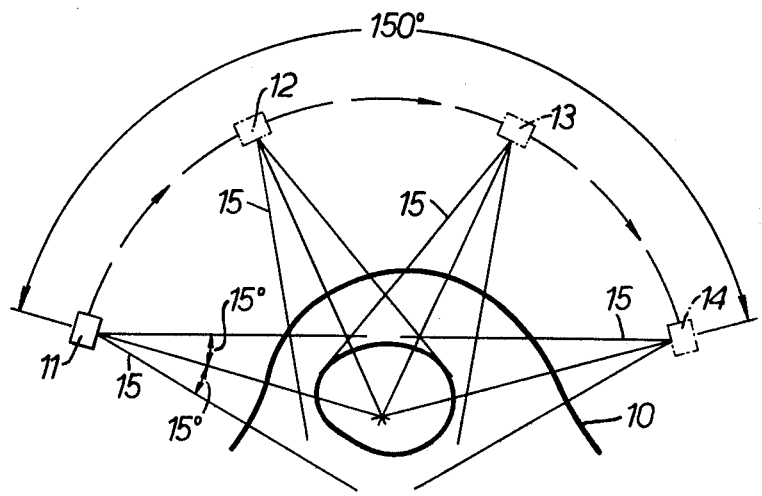
FIG. 1 illustrates a typical compound scan of a patient using a 150° arc scan and a ±15° sector scan.

Referring to the Figures in more detail, FIG. 1 illustrates a typical compound scan of an object 10 by means of a single transducer 11 which is moved to a number of positions 11, 12, 13 and 14 during examination of the object 10. At each of these positions, pulses of ultrasound are transmitted by the transducer 11 along a plurality of beams 15 into the object 10, and reflected echoes received along these beams. In an alternative compound scan of the object 10, a plurality of transducers 11,12,13 and 14 which are spatially positioned with respect to the object 10, and each transducer is activated along a plurality of beams 15. The formation of a compound scan by use of such a plurality of transducers is disclosed in Australian Patent Specification No. 56559/73.

Figure 2:
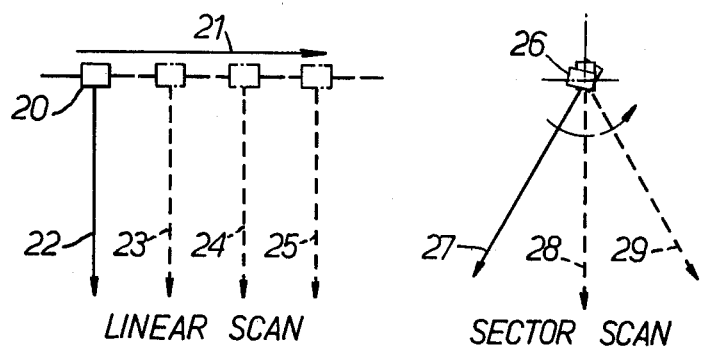
FIG. 2 illustrates typical simple scans.

FIG. 2 illustrates typical simple scan modes which may be utilised to form a second display in accordance with the present invention. In the linear scan mode, transducer 20 is moved relative to the object under examination in the direction of the arrow 21, and pulses of ultrasound transmitted into the object, and echoes received, along a plurality of beams 22,23, 24 and 25. In the sector scan mode, a single transducer 26 is mechanically oscillated or electronically steered to direct pulses of ultrasound and receive echoes along a plurality of beams 27,28 and 29.

Figure 3:
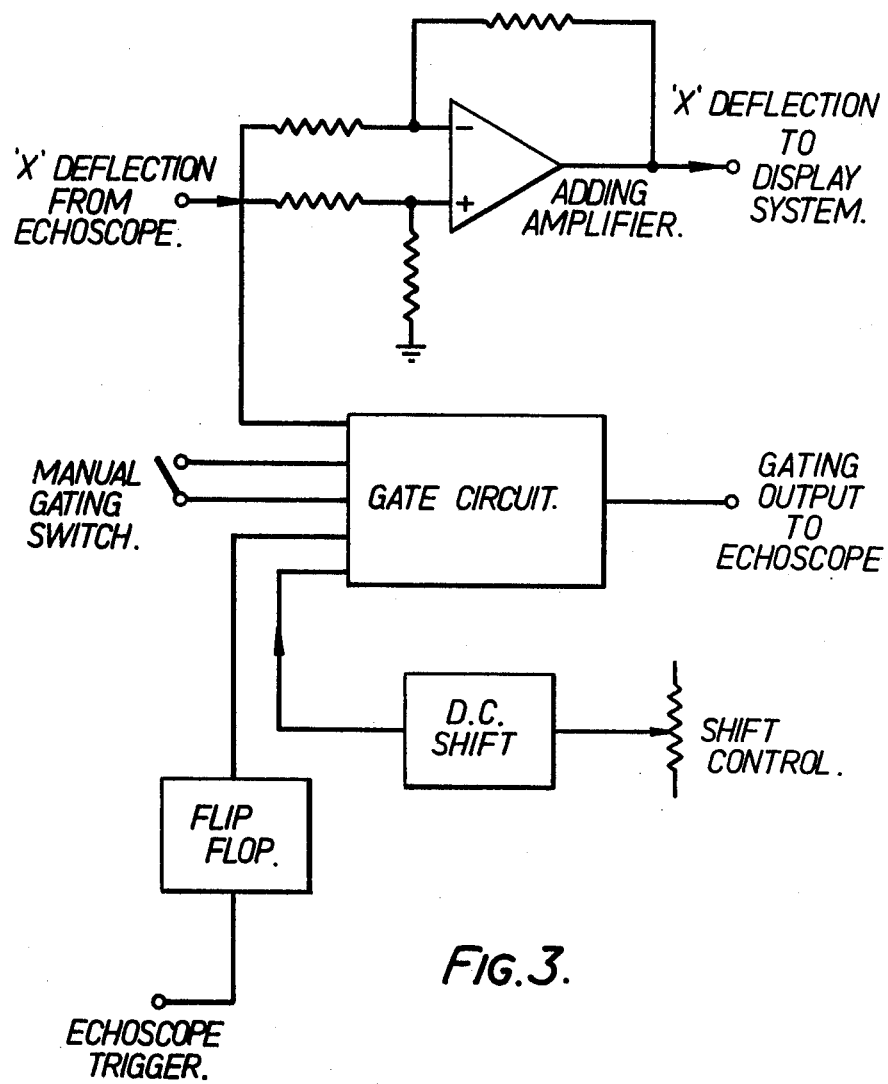
FIG. 3 illustrates one embodiment of the present invention whereby a simultaneous side-by-side display of a compound and a simple scan may be achieved.

The circuit illustrated in FIG. 3 is intended for use with either of the two methods described above for performing this invention utilising a single transducer echoscope and for simultaneous display of a compound scan and a simple scan on a high quality display unit. As an example of such a display unit, a scan converter display system is suitable as it has a resolution of over 2000 lines whereas each ultrasound scan only requires a resolution of the order of 400 lines. An ultrasound scan is displayed by applying appropriate X and Y signals to the display unit to represent the line of sight of each ultrasound pulse that is sent into the object under examination, such as a patient, and a Z signal which gives the brightness of the echoes along this line of sight. In the embodiment illustrated in FIG. 3, in order to produce part of the scan to one side of the compound scan, it is necessary to shift the X deflection signal by adding a fixed DC voltage during the lines of sight that are required for the simple scan. In FIG. 3 the X signal passes through a unity gain amplifier in which a D.C. shift voltage can be added to it. This addition of the D.C. voltage is controlled by the gating circuit and its manual switch. The manual switch is operated during the time of the simple scan that is desired and this is removed from the compound scan. If however the echoscope trigger is fed into this circuit its frequency will be divided by two by the flip flop before it is fed into the gating circuit and hence only every second pulse will be removed for display in the simple scan during the time that the manual switch is operated. In the case of the multi-transducer echoscope mentioned previously, the trigger signal must come from the transducer which has been selected to produce the simple scan and is therefore being pulsed twice as often as is normal. The gating circuit also puts out a signal to the echoscope to indicate which particular pulses are being used for the simple scan so that any parameters, such as the video level, may be altered. Clearly it is possible to place the simple scan display above or below the compound scan by substituting the Y for the X deflection signal in the description above. It will also be apparent that other features of the echoscope and display unit which are used in this embodiment are well known in the art.

The foregoing description sets out a number of alternative methods by which the present invention may be applied to ultrasonic scanning equipment in order to overcome the problem of the prior art where compound and simple scans were taken at different times and hence there was no guarantee that exactly the same section was being displayed in both scans. All such alternatives are encompassed within the concept of the present invention.

The claims defining the invention are as follows:

1. A method of displaying information obtained by ultrasonic echoscopic examination of an object, said examination comprising the steps of transmitting pulses of ultrasonic energy along a plurality of beams into the said object and receiving echoes of said pulses reflected along said beams by acoustic impedance discontinuities within the object, said beams being directed from a plurality of spaced positions relative to said object and along a plurality of beam directions at each said position, said pulses being transmitted and said echoes being received along said plurality of beams by activation of a single transducer which is moved to said plurality of spaced positions during said examination of the object, which method comprises forming a first display of information representative of the position of acoustic impedance discontinuities within said object from said echoes received along said plurality of beams, and forming a second display of information from echoes received along every alternate beam in sequence within a selected group of said plurality of beams.

2. A method of displaying information obtained by ultrasonic echoscopic examination of an object, said examination comprising the steps of transmitting pulses of ultrasonic energy along a plurality of beams into the said object and receiving echoes of said pulses reflected along said beams by acoustic impedance discontinuities within the object, said beams being directed from a plurality of spaced positions relative to said object and along a plurality of beam directions at each said position, said pulses being transmitted and said echoes being received along said plurality of beams by activation of a plurality of transducers, each of which is positioned at one of said plurality of spaced positions, a selected one or ones of said transducers being activated to transmit twice the number of said pulses of ultrasonic energy into the object as are transmitted by the others of said transducers, which method comprises forming a first display of information representative of the position of acoustic impedance discontinuities within said object from said echoes received along said plurality of beams, and forming a second display of information from echoes received along every alternate beam in sequence produced by said selected transducer or transducers.

3. Apparatus for the ultrasonic echoscopic examination of an object, comprising:
   transducer means for transmitting pulses of ultrasonic energy along a plurality of beams into the said object and receiving echoes of said pulses reflected along said beams by acoustic impedance discontinuities within the object, said transducer means directing said beams from a plurality of spaced positions relative to said object and along a plurality of beam directions at each said position, said transducer means comprising a single transducer which is moved to said plurality of spaced positions during said examination of the object;
   means for forming a first display of information representative of the position of acoustic impedance discontinuities within said object from said echoes received along said plurality of beams;
   means for selecting beams from said plurality of beams, said means for selecting beams comprising means for selecting every alternate beam in sequence within a selected group of said plurality of beams; and
   means for forming a second display of information from echoes received along said selected beams.

4. Apparatus for the ultrasonic echoscopic examination of an object, comprising:
   transducer means for transmitting pulses of ultrasonic energy along a plurality of beams into the said object and receiving echoes of said pulses reflected along said beams by acoustic impedance discontinuities within the object, said transducer means directing said beams from a plurality of spaced positions relative to said object and along a plurality of beam directions at each said position, said transducer means comprising a plurality of transducers, each of which is positioned at one of said plurality of spaced positions;
   means for forming a first display of information representative of the position of acoustic impedance discontinuities within said object from said echoes received along said plurality of beams;
   means for selecting beams from said plurality of beams, said means for selecting beams comprising means for activating a selected one or ones of said transducers to transmit twice the number of said pulses of ultrasonic energy into the object as are transmitted by the others of said transducers, and means for selecting every alternate beam in sequence produced by said selected transducer or transducers; and
   means for forming a second display of information from echoes received along said selected beams.

5. Apparatus for the ultrasonic echoscopic examination of an object, comprising:
   transducer means for transmitting pulses of ultrasonic energy along a plurality of beams into the said object and receiving echoes of said pulses reflected along said beams by acoustic impedance discontinuities within the object, said transducer means directing said beams from a plurality of spaced positions relative to said object and along a plurality of beam directions at each said position;
   means for forming a first display of information representative of the position of acoustic impedance discontinuities within said object from said echoes received along said plurality of beams;
   means for selecting beams from said plurality of beams; and
   means for forming a second display of information from echoes received along said selected beams, said means for forming a first display and said means for forming a second display comprising a single display unit, said means for forming a second display comprising means to vary signals to said display unit associated with said selected beams by a constant amount to form said second display separate from said first display.

* * * * *